United States Patent
Gross et al.

[11] Patent Number: 5,882,516
[45] Date of Patent: Mar. 16, 1999

[54] DIALYZER

[75] Inventors: Arnold Gross, Oberkirchen; Gerhard Wiesen, St. Wendel, both of Germany

[73] Assignee: Fresenius AG, Bad Homburg, Germany

[21] Appl. No.: 805,705

[22] Filed: Feb. 25, 1997

[30] Foreign Application Priority Data

Feb. 26, 1996 [DE] Germany ............ 196 07 162.3

[51] Int. Cl.⁶ ............ B01D 61/28; B01D 63/02; B01D 63/04
[52] U.S. Cl. ............ 210/321.6; 210/321.64; 210/321.72; 210/321.79; 210/321.8; 210/321.81; 210/321.88; 210/321.89; 210/321.9
[58] Field of Search ............ 210/645, 646, 210/650, 651, 321.6, 321.61, 321.64, 321.72, 321.78, 321.79, 321.8, 321.81, 321.87, 321.88, 321.89, 321.9, 433.1, 500.23; 604/4, 5; 422/44, 45, 48

[56] References Cited

U.S. PATENT DOCUMENTS

| | | | |
|---|---|---|---|
| 4,702,829 | 10/1987 | Polaschegg et al. | 210/321.72 |
| 4,861,485 | 8/1989 | Fecondini | 210/646 |
| 5,178,763 | 1/1993 | Delaunay | 210/646 |
| 5,192,499 | 3/1993 | Sakai et al. | 210/321.89 |
| 5,476,592 | 12/1995 | Simard | 210/651 |

FOREIGN PATENT DOCUMENTS

| | | |
|---|---|---|
| 36 34 763 | 9/1989 | Germany . |
| 34 48 262 | 6/1990 | Germany . |

*Primary Examiner*—John Kim
*Attorney, Agent, or Firm*—Kenyon & Kenyon

[57] ABSTRACT

The invention relates to a dialyzer comprised of two modules that are realized in one basic unit. The first module has a bundle of membrane capillaries and one inlet and one outlet each for the fluid to be treated and one inlet and one outlet for the dialysate. The second module likewise comprises a bundle of membrane capillaries used to sterilize substituate by filtration and one inlet for the substituate. In addition, the dialyzer has a chamber, in which the purified substituate is able to be combined with the fluid to be treated.

8 Claims, 3 Drawing Sheets

DIALYZER

FIELD OF THE INVENTION

The invention relates to a dialyzer, which is intended for use, in particular, in hemodiafiltration processes.

BACKGROUND INFORMATION

Hemodiafiltration is a combined process in which hemodialysis and hemofiltration are carried out simultaneously. This process unites the advantages associated with convective mass transfer in hemofiltration and those of the dialytic diffusion process. To implement volumetric fluid balancing in known on-line hemodiafiltration processes, balancing chambers are utilized to directly measure a replacement fluid (substituate). Thus, a patient's fluid intake and output is centrally controlled by means of the balancing chambers, while all added and withdrawn fluids are observed. Also in an on-line process, no additional reservoir is needed for the substituate, because it is produced concurrently. In the known process, the substituate is sterilized by filtration using an especially provided on-line hemodiafiltration filter, which is present in addition to the actual hemodiafiltration filter. The additionally provided on-line hemodiafiltration filter is not replaced with every treatment. For that reason a separate contamination-prevention chamber is provided to reduce the risk of cross-contamination. In spite of this measure, there is still a residual risk of cross-contamination.

SUMMARY OF THE INVENTION

An object of the invention is to devise a dialyzer which will make it possible to substantially avoid the aforementioned risk of cross-contamination and, in addition, simplify the assembly and operation of the hemodiafiltration system.

The dialyzer of the present invention is comprised of two modules that are realized in one basic unit, the first module having a bundle of membrane capillaries and one inlet and one outlet each for the fluid to be treated and one inlet and one outlet for the dialysate. The second module likewise comprises a bundle of membrane capillaries used to sterilize a substituate by filtration and one inlet for the substituate. The dialyzer has a chamber, in which the purified substituate is able to be combined with the fluid to be treated, i.e. the blood.

Thus, the dialyzer of the invention unites a standard hemodialysis unit and a unit for sterilizing the substituate by filtration that is needed for the on-line hemodiafiltration. The entire dialyzer is conceived as a disposable part, so that it is no longer necessary to disinfect the module, and damages to the housing or membrane caused by disinfection are avoided, as are residues that might otherwise be infused. In particular, the danger of cross-contamination that existed in the previously known system is eliminated.

A further advantage of the invention is that the need for performing a preliminary seal-tightness test on the on-line filter used for the substituate has been eliminated, the on-line filter having previously been provided as a separate unit. This results in a shorter preparation time and, therefore, in increased availability. Compared to the known system elucidated at the outset that required a repeated dead-end filtration, a concentration of endotoxins is no longer possible.

Also, since the entire dialyzer is conceived as a disposable part, there is no chance of an uncontrolled use that exceeds the recommended service life. Therefore, operating errors are precluded and all time- and cycle-critical states are eliminated. It is now possible to have a very simply designed tubular system to convey the substituate to be sterilized by filtration. The contamination prevention chamber needed in the earlier system can be eliminated. The dialyzer is compatible with all tubular systems and machines. Finally, by dispensing with an additional on-line filter, a suspension mount and its requisite space are economized, so that the overall system has a simpler and more logical design.

In accordance with one advantageous refinement of the invention, the dialyzer is comprised of an elongated housing, which is sealed at both of its ends by covers. The two modules in the elongated housing are divided by a separating wall. The membrane capillaries arranged in the modules in the longitudinal direction of the housing are embedded in each case in sealing compound, which seals off the open ends of the elongated housing. The capillaries of the membrane-capillary bundle in the first module can thereby extend with their front-side, open ends through the sealing compound. The capillaries of the membrane capillary bundle in the second module can extend with their first, front-side, open ends through the sealing compound, while their opposite, second, front-side, open ends are embedded in the sealing compound, thereby sealing them off. Alternatively, the first and second ends of the capillaries can extend through the sealing compound. In this specific embodiment, the second ends can be sealed off, for example, by a properly adapted cover. These arrangements enable the substituate in the second module to be sterilized by filtration through the membrane capillaries and to be purified through the first open ends of the membrane capillaries with the fluid to be treated, in other words the blood.

The membrane capillaries arranged in the second module can thereby open through with their first open ends into a chamber formed between the sealing compound and the cover, i.e., the flanged space, the cover being joined to the inlet for the fluid to be treated, i.e., the blood. This is known as pre-dilution.

On the other hand, the membrane capillaries arranged in the second module can open through with their first open end into a chamber formed between the sealing compound and the cover, i.e., the flanged space, the cover being joined to the outlet for the fluid to be treated. In this case, a post-dilution takes place.

Especially advantageous is the use of the dialyzer according to the invention in an on-line hemodiafiltration process.

DETAILED DESCRIPTION

Figure 1:
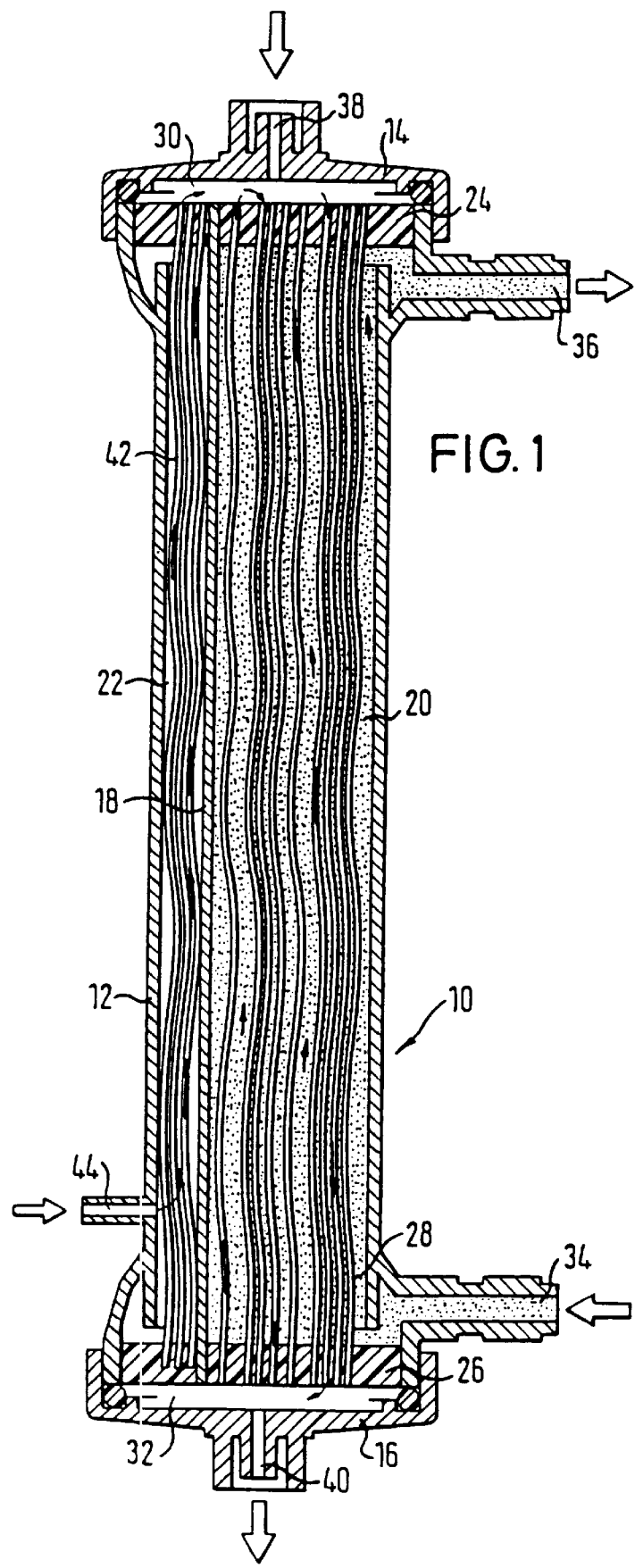
FIG. 1 shows a longitudinal section through a first specific embodiment of the dialyzer according to the present invention.

Dialyzer 10 in accordance with the specific embodiment shown in FIG. 1 comprises a cylindrical and an elongated housing 12, which is sealed at the ends by covers 14 and 16. The elongated housing is subdivided by a separating wall 18 into two modules 20 and 22. Modules 20 and 22 are both delimited, on the one hand, by the separating wall and the outer wall of housing 12 and, on the other hand, by sealing compounds 24 and 26, which seal off housing 12 at the extremity. Module 20 comprises in a generally known way, a microcapillary bundle having microcapillaries 28, which, as shown in FIG. 1, run along elongated housing 12 and are embedded in sealing compounds 24 and 26 so as to allow their open ends to open through in each case into cavities or chambers 30, 32 formed between sealing compounds 24 and 26 and covers 14 and 16, respectively. Module 20 has one inlet 34 and one outlet 36 for the dialysate in the manner depicted in FIG. 1. An inlet 38 for the blood is formed in the center of cover 14, while an outlet 40 for the blood is formed in the center of cover 16.

Module 22 also has a capillary bundle comprised of membrane capillaries 42. These membrane capillaries 42 likewise extend in an elongated form to cylindrical housing 12. They are embedded at one extremity in sealing compound 26 so as to seal them off. Membrane capillaries 42 are embedded at their opposite extremity in sealing compound 24, but open with their ends toward chamber 30 between sealing compound 24 and cover 14.

In the case of the dialyzer illustrated in FIG. 1, the blood to be purified enters into inlet 38 and is united in chamber 30 with substituate that has been sterilized by filtration. The blood, mixed with the substituate, enters into membrane capillaries 28 and passes through said capillaries up to their opposite extremity which opens through into chamber 32. The purified blood emerges above chamber 32 and outlet 40. Within module 20, the dialysate is fed in via the corresponding inlet 34 and runs in counter flow to the blood to be purified, until it emerges again out of outlet 36 at the opposite end of module 20. In module 22, the substituate to be treated enters in the direction shown by the arrow via an inlet 44. Within module 22, the substituate to be purified is sterilized by filtration by way of membrane capillaries 42. The substituate that has been sterilized by filtration emerges at the open end of the membrane capillaries, as previously described, into chamber 30 and is mixed there with the blood to be treated. The arrows in FIG. 1 indicate the direction of each of the fluid flows. In the exemplary embodiment of FIG. 1, where the substituate is united with the in-flowing blood that is still to be purified, a pre-dilution is realized.

Figure 2:
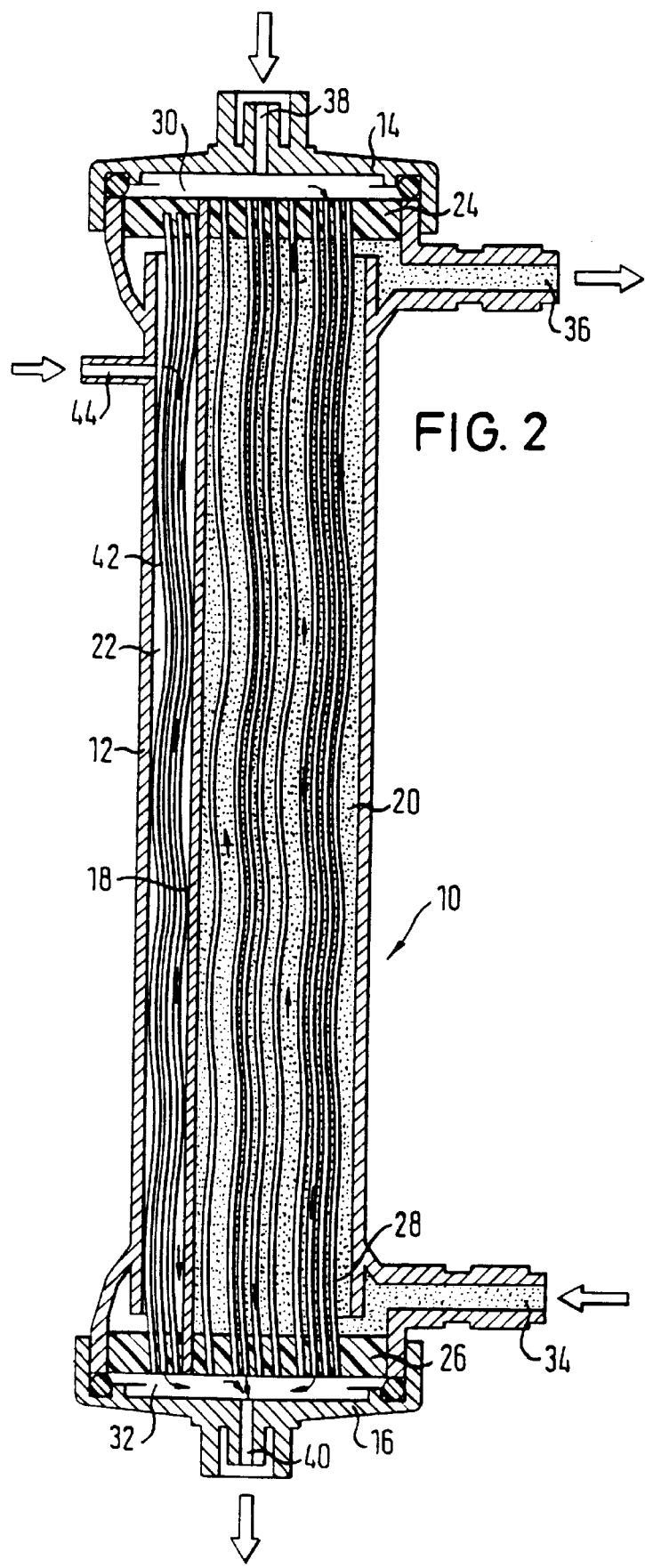
FIG. 2 shows a longitudinal section through a second specific embodiment of the dialyzer according to the present invention.

The exemplary embodiment in accordance with FIG. 2 substantially corresponds to that of FIG. 1. Therefore, the same parts are denoted by the same reference numerals. In particular, the overall design of housing 12 and of covers 14 or 16, as well as of module 20 corresponds to the previously described exemplary embodiment. However, the exemplary embodiment differs in the design of second module 22. In this case, the open ends of the capillaries open through into chamber 32, which is formed between sealing compound 26 and cover 16. The opposite extremity of the membrane capillaries is embedded in sealing compound 24 so as to seal off the ends. Furthermore, in contrast to the exemplary embodiment of FIG. 1, inlet 44 for the substituate to be purified is disposed on the opposite side of elongated housing 12, so that, in this specific embodiment as well, the substituate to be purified flows to the extent that is possible over the entire length of housing 12 (compare arrow direction) and can be purified along this path, in other words sterilized by filtration, by means of the membrane walls. In this exemplary embodiment, the purified blood is united with the substituate in chamber 32, so that a post-dilution is realized.

Figure 3:
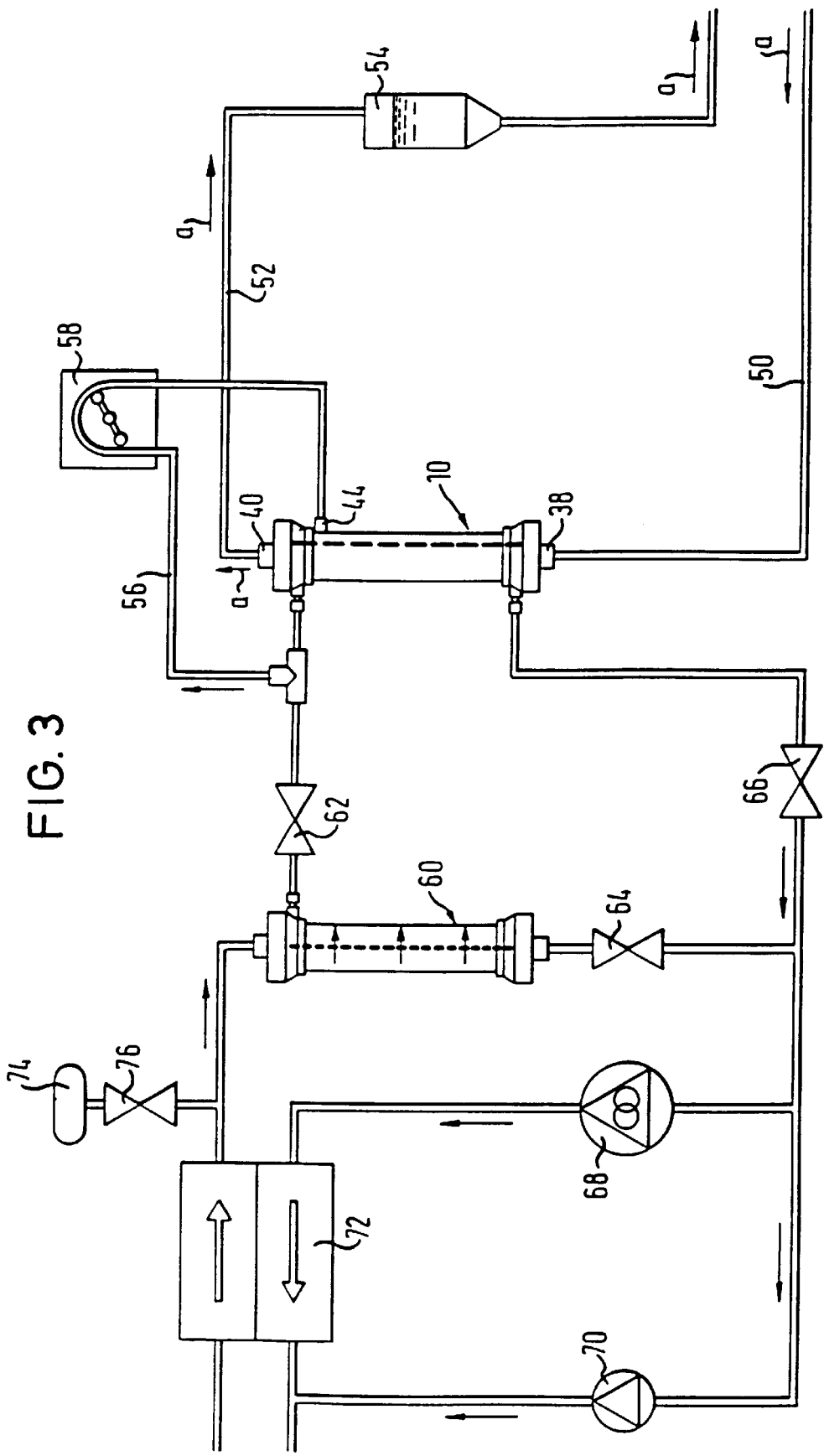
FIG. 3 shows a system plan of an on-line hemodiafiltration device including a dialyzer installed therein according to the present invention.

FIG. 3 shows the basic design layout of an on-line hemodiafiltration system. The blood drawn from the patient is supplied in arrow direction "a" via a line 50 to inlet 38 of dialyzer 10. The purified blood is directed in arrow direction a, via outlet 40 and line 52, into a drip chamber 54, from where it is supplied to the patient again. The substituate is fed via a line 56 and a substituate pump 58 into inlet 44 of dialyzer 10. The part of the on-line hemodiafiltration system in accordance with FIG. 3, which relates to the preparation of the dialysate, corresponds to previously known systems. Thus, this part comprises a dialyzing fluid filter 60, a dialyzer valve 62, a bypass valve 64, a valve 66, a dialysate flow pump 68, a UF pump 70, a balancing chamber 72, a hydrophobe filter 74 and a ventilating valve 76.

The on-line hemodiafiltration system in accordance with FIG. 3 enables processes which are clearly simplified over previously known processes because of the use of dialyzer 10 of the invention, since there is no longer a need in this case for a separate filter for the substituate and for an additional anti-contamination chamber arranged downstream from said chamber.

What is claimed is:

1. A dialyzer comprising:
an elongated housing having a first end and a second end, wherein the elongated housing is sealed at the first and second ends;
a first and a second module located within the elongated housing, the first and second modules being separated from one another by a separating wall;
the first module including:
a plurality of membrane capillaries for cooperating with a fluid to be treated, the membrane capillaries being secured in the first module by a sealing compound and arranged in a direction longitudinal to the elongated housing, the membrane capillaries in the first module including first and second open ends extending through the sealing compound located adjacent the first and second ends of the elongated housing,
a first inlet port and a first outlet port for the fluid, and a second inlet port and a second outlet port for cooperating with a dialysate;
the second module including:
an inlet port for receiving a substituate, and a plurality of membrane capillaries secured in the second module for purifying the substituate by filtration, the plurality of membrane capillaries in the second module secured by a sealing compound and arranged in a longitudinal direction to the elongated housing, the plurality of membrane capillaries in the second module including third open ends extending through the sealing compound at the first end of the elongated housing and fourth open ends embedded in the sealing compound at the second end of the elongated housing to seal the plurality of membrane capillaries in the second module; and
a chamber for combining the purified substituate with the fluid.

2. The dialyzer according to claim 1, wherein the fourth open ends extend through the sealing compound at the second end of the elongated housing, and wherein the fourth open ends of the plurality of membrane capillaries in the second module are sealed with a cover.

3. The dialyzer according to claim 2, wherein the third open ends of the plurality of membrane capillaries in the second module extend into a chamber formed between the sealing compound at the first end of the elongated housing and a cover, the cover being connected to the inlet for the fluid to be treated.

4. The dialyzer according to claim 1, wherein the third open ends of the plurality of membrane capillaries in the second module extend into a chamber formed between the sealing compound at the first end of the elongated housing and a cover, the cover being connected to the inlet for the fluid to be treated.

5. The dialyzer according to claim 1, wherein the plurality of membrane capillaries in the second module include third open ends embedded in the sealing compound at the first end of the elongated housing to seal the plurality of membrane capillaries in the second module, and wherein the plurality of membrane capillaries in the second module further include fourth open ends extending through the sealing compound at the second end of the elongated housing.

6. The dialyzer according to claim 5, wherein the fourth open ends of the plurality of membrane capillaries in the second module extend into a chamber formed between the sealing compound at the second end of the elongated housing and a cover, the cover being connected to the outlet for the fluid.

7. The dialyzer according to claim 1, wherein the plurality of membrane capillaries in the second module include third and fourth open ends extending through the sealing compounds at the first and second ends of the elongated housing, and wherein the third open ends of the plurality of membrane capillaries in the second module are sealed with a cover.

8. The dialyzer according to claim 7, wherein the fourth open ends of the plurality of membrane capillaries in the second module extend into a chamber formed between the sealing compound at the second end of the elongated housing and a cover, the cover being connected to the outlet for the fluid.

* * * * *